(12) United States Patent
Stroganov et al.

(10) Patent No.: US 9,983,123 B2
(45) Date of Patent: May 29, 2018

(54) ABSORPTION ANALYZER

(71) Applicants: Alexander Anatolevich Stroganov, St. Petersburg (RU); Sergey Evgenevich Sholupov, St. Petersburg (RU); Sergey Evgenevich Pogarev, St. Petersburg (RU); Alexander Ahatovich Ganeev, Pushkin St. Petersburg (RU); Vladimir Veniaminovich Rhyzov, St. Petersburg (RU)

(72) Inventors: Alexander Anatolevich Stroganov, St. Petersburg (RU); Sergey Evgenevich Sholupov, St. Petersburg (RU); Sergey Evgenevich Pogarev, St. Petersburg (RU); Alexander Ahatovich Ganeev, Pushkin St. Petersburg (RU); Vladimir Veniaminovich Rhyzov, St. Petersburg (RU)

( * ) Notice: Subject to any disclaimer, the term of this patent is extended or adjusted under 35 U.S.C. 154(b) by 0 days. days.

(21) Appl. No.: 15/324,786

(22) PCT Filed: Jul. 3, 2015

(86) PCT No.: PCT/RU2015/000417
§ 371 (c)(1),
(2) Date: Jan. 9, 2017

(87) PCT Pub. No.: WO2016/007048
PCT Pub. Date: Jan. 14, 2016

(65) Prior Publication Data
US 2017/0199119 A1 Jul. 13, 2017

(30) Foreign Application Priority Data
Jul. 9, 2014 (RU) ................................ 2014128237

(51) Int. Cl.
*G01J 3/30* (2006.01)
*G01N 21/33* (2006.01)
(Continued)

(52) U.S. Cl.
CPC ......... *G01N 21/33* (2013.01); *G01N 21/3103* (2013.01); *G01N 33/0047* (2013.01)

(58) Field of Classification Search
CPC . G01N 21/33; G01N 21/3103; G01N 33/0047
(Continued)

(56) References Cited

U.S. PATENT DOCUMENTS

2004/0245470 A1* 12/2004 Nadezhdinskii ....... G01N 21/39
250/343
2011/0026020 A1* 2/2011 Sholupov ........... G01N 21/3103
356/313

* cited by examiner

*Primary Examiner* — Hina F Ayub
(74) *Attorney, Agent, or Firm* — Walker & Jocke

(57) ABSTRACT

The invention relates to analytical chemistry, in particular, to the spectral absorption analysis with a differential method of measuring concentrations of mercury and benzene vapors. The invention is aimed at creation of an absorption analyzer, which allows to determine the content of mercury and benzene in the carrier gas, with improved analytical performance for benzene.
The aim is achieved with an absorption analyzer, which comprises optically coupled components: a photodetector, an analytical cell, a modulator of radiation polarization and a spectral lamp containing a discharge cavity located between magnet poles and connected with means of electric discharge excitation, buffer gas and mercury placed into the spectral lamp, as well as a gas system connecting a sampling port of the analyzer with an input port of the analytical cell by gas communications, wherein the gas system comprises at least three gas channels connecting the sampling port of the analyzer to the input port of the analytical cell via a gas (Continued)

Figure 1:
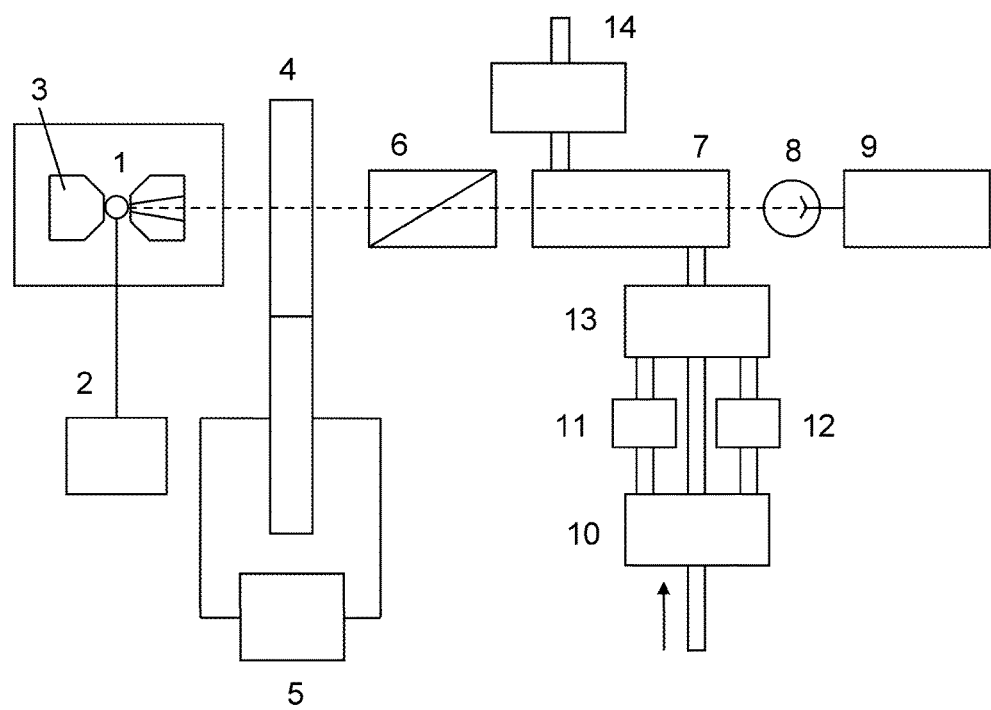

channels selector, while at least one of these gas channels comprises means for removing the benzene from the gas stream, at least one comprises means for removing mercury from the gas stream, at least one is permeable for mercury, at least one is permeable for benzene and at least one has different permeability rates for mercury and benzene.

12 Claims, 3 Drawing Sheets

(51) Int. Cl.
    *G01N 33/00*     (2006.01)
    *G01N 21/31*     (2006.01)

(58) Field of Classification Search
    USPC ........................................................ 356/313
    See application file for complete search history.

ABSORPTION ANALYZER

The invention relates to analytical chemistry, in particular, to the spectral absorption analysis with a differential technique of measurement of mercury and benzene vapors concentration and can be used to create a device that allows measurement of the mercury and benzene content in a carrier gas and to reduce benzene detection limit substantially.

STATE OF THE ART

A benzene absorption analyzer with an atomic line frequency tunable by magnetic field is known (1, 2), which contains a spectral mercury lamp placed in a constant magnetic field, a lens, an analytical cell, a polarization modulator, a monochromator and a photodetector. The polarization modulator alternately transmits radiation of Zeeman components, one of which coincides with a local maximum of benzene absorption band, and the other is outside it. Then, intensity of one of Zeeman components depends on the optical density of benzene molecules and background absorption, while intensity of the other one depends on the absorbance of only background absorption. These two measurements allows to calculate the value of the optical density of benzene molecules, which is related with a benzene concentration by the calibration expression.

The drawbacks of the analog are high detection limit of benzene in the air (1,000 mg/m3), which does not allow to use it for solving practical tasks (3), because the Occupational Exposure Limit is 3.2 mg/m3, as well as weight and power consumption are too large for portable analyzers.

The closest prototype to the proposed invention in terms of its technical essence is an atomic absorption mercury analyzer with Zeeman correction of background absorption (4) consisting of a spectral mercury lamp placed between the poles of a magnet, a modulator of radiation polarization, analytical cell, a photodetector and a signal processing unit. This scheme implements the method of differential atomic absorption spectroscopy. Observation along the magnetic field lines allows to detect only σ-components of the Zeeman triplet, with one σ-component being in the area of a maximum of the absorption line and performing a role of an analytical line and the other being at the edge of the absorption line envelope, where the absorption cross section is much less than in the maximum and performing the role of a reference line. In the signal-processing block two signals are selected: the first one—at the modulation frequency and the second one—at direct current. The first signal is proportional to the concentration of mercury atoms in the analytical cell and the second signal is proportional to the total intensity of the σ-components. Further processing of the signals occurs in the microprocessor according to a known algorithm (5).

The drawbacks of the prototype should include a strong influence of benzene on the result of mercury content determination in the sample gas, which is particularly important in natural gas analysis.

ESSENCE OF THE INVENTION

The invention is aimed at creation of an absorption analyzer, which allows to determine the content of mercury and benzene in the carrier gas, with improved analytical performance for benzene, namely, with a detection limit below the Occupational Exposure Limit of benzene in the air of the working area.

The aim is achieved with an absorption analyzer, which comprises optically coupled components: a photodetector, an analytical cell, a modulator of radiation polarization and a spectral lamp containing a discharge cavity located between magnet poles and connected with means of electric discharge excitation, buffer gas and mercury placed into the spectral lamp, as well as a gas system connecting a sampling port of the analyzer with an input port of the analytical cell by gas communications, wherein the gas system comprises at least three gas channels connecting the sampling port of the analyzer to the input port of the analytical cell via a gas channels selector, while at least one of these gas channels comprises means for removing the benzene from the gas stream, at least one comprises means for removing mercury from the gas stream, at least one is permeable for mercury, at least one is permeable for benzene and at least one has different permeability rates for mercury and benzene.

The absorption analyzer also contains mercury in the spectral lamp, which is enriched with mercury isotope with an even number of neutrons, wherein said isotope constitutes not less than 50% of the total amount of mercury in the spectral lamp.

The main idea of the invention consists in the following. It is known that benzene has a strong absorption band at the range of 227.0-267.0 nm with a partially resolved vibrational-rotational structure (6). This spectral range contains the resonance line of mercury $\lambda$=254 nm. Therefore, it is possible to use a single radiation source—a spectral mercury lamp, and to determine concentrations of mercury and benzene by means of absorption spectrometry with direct Zeeman effect using mercury resonance line $\lambda$=254 nm. To do this, a magnitude of the magnetic field applied to a mercury lamp, is chosen so that one σ-component of the resonance emission line of mercury is shifted into an area of a maximum of the resonance absorption line of mercury and at the same time is within a range of a local maximum of the absorption band of benzene. This component performs a role of the analytical line. Other σ-component of the mercury emission line is at a slope of the mercury absorption line profile and at the same time it is out of the local maximum of the benzene absorption band, where the absorption cross sections for both substances are smaller than their maximal values. The second component plays a role of the reference line. Further signals processing uses known algorithm for differential absorption spectrometry (5). Separation of signals from mercury and benzene is carried out by means of two measurements. In the first measurement a sample gas is transmitted directly into the analytical cell and the measured signal is equal to the sum of signals from mercury and benzene, $S_1=S_{Hg}+S_{benzene}$. In the second measurement the sample gas is transmitted into the analytical cell through a gas filter which removes mercury from the gas stream, and the measured signal is equal to the concentration of benzene in the gas, $S_2=S_{benzene}$. Thus, the benzene concentration is $C_{benzene}=a_{benzene}*S_2$, and the mercury concentration is $C_{Hg}=a_{Hg}*(S_1-S_2)$, where $a_{benzene}$ and $a_{Hg}$ are calibration coefficients respectively.

The use of mercury enriched with one of the isotopes in the spectral lamp can reduce the limit of detection for both mercury and benzene, due to the increase of the differential cross section of absorption. Table 1 shows the relative differential cross section for mercury and benzene absorption at magnetic field of 0.51 T in a spectral lamp using different mercury isotopic composition.

TABLE 1

| The isotopic composition | Benzene ($\Delta Q/Q_{202}$) | Mercury ($\Delta Q/Q_{202}$) |
|---|---|---|
| $^{204}$Hg | 0.052 | 0.59 |
| $^{202}$Hg | 0.01 | 0.08 |
| $^{200}$Hg | — | 0.53 |
| $^{198}$Hg | 0.019 | 0.82 |
| $^{196}$Hg | 0.041 | 1.00 |
| Natural mixture | 0.016 | 0.2 |

Since odd mercury isotopes have hyper fine components located on both sides relative to the maximum of the absorption line profile of mercury and benzene, it is obvious that the differential cross section of absorption in the longitudinal geometry (observing the radiation along the magnetic field) for them is small. From the data shown above it is seen that in the case of mercury in the spectral lamp enriched with $^{204}$Hg, the differential cross section of absorption is greater about 3 times for both mercury and benzene in comparison with a lamp with natural mercury composition. The degree of mercury concentration should not be below 50%, otherwise there is a reduction of the differential absorption cross section. For example, if the mercury contains 50% of $^{204}$Hg and 50% of $^{198}$Hg, the calculation shows that the value of the maximum differential cross section drops 2.5 times in comparison with the mono isotopic $^{204}$Hg and becomes close to the maximum value of the differential cross section for mercury with natural composition.

The essence of the claimed invention is illustrated by figures:

FIG. 1. A block diagram of an absorption analyzer.

Figure 2:
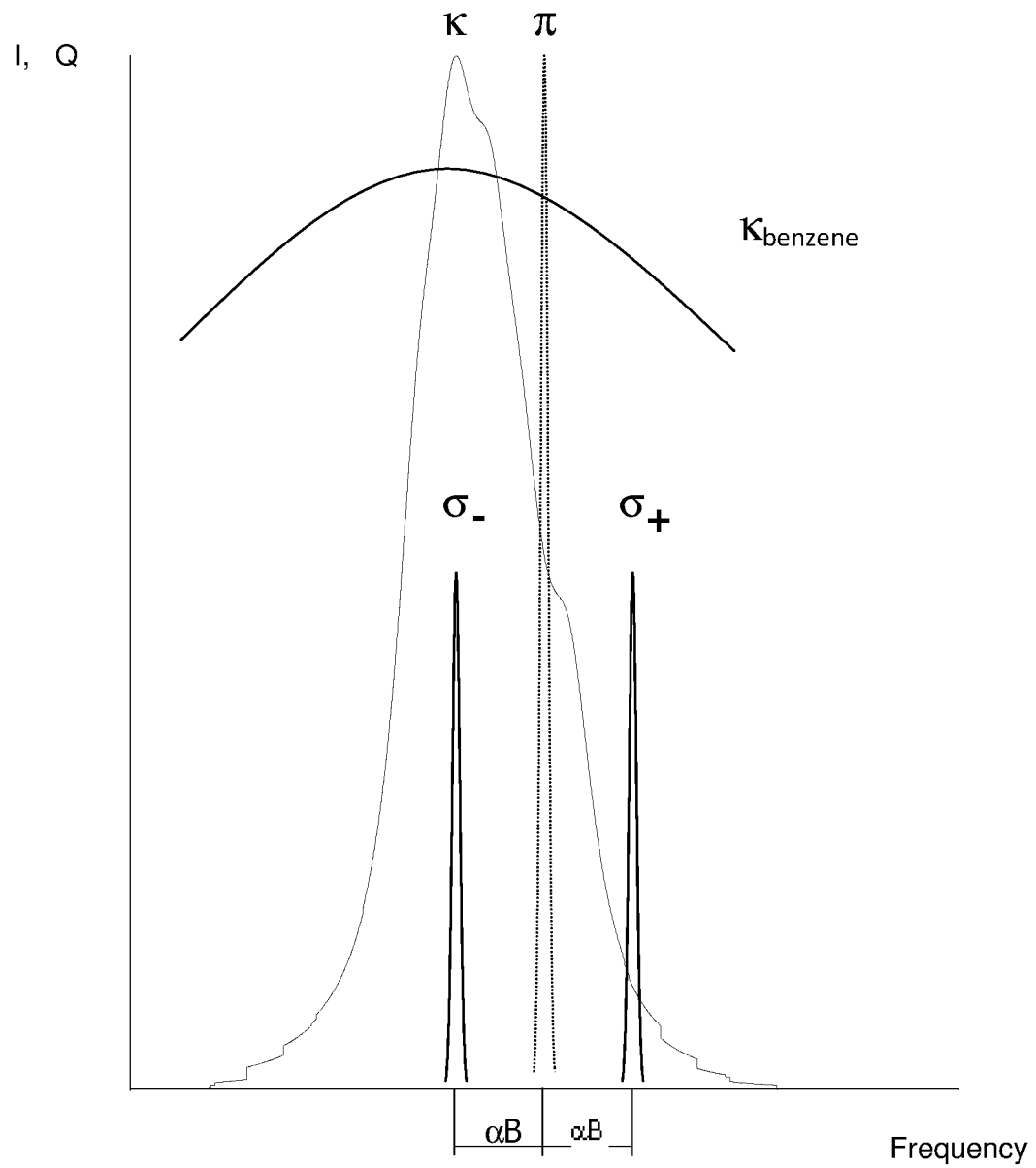

FIG. 2. The diagram of spectral location of Zeeman π- and $\sigma_\pm$-emission line—components $^{198}$Hg λ=254 nm absorption line profile of mercury (κ) and benzene absorption bands (κbenzene) (atmospheric pressure).

Figure 3:
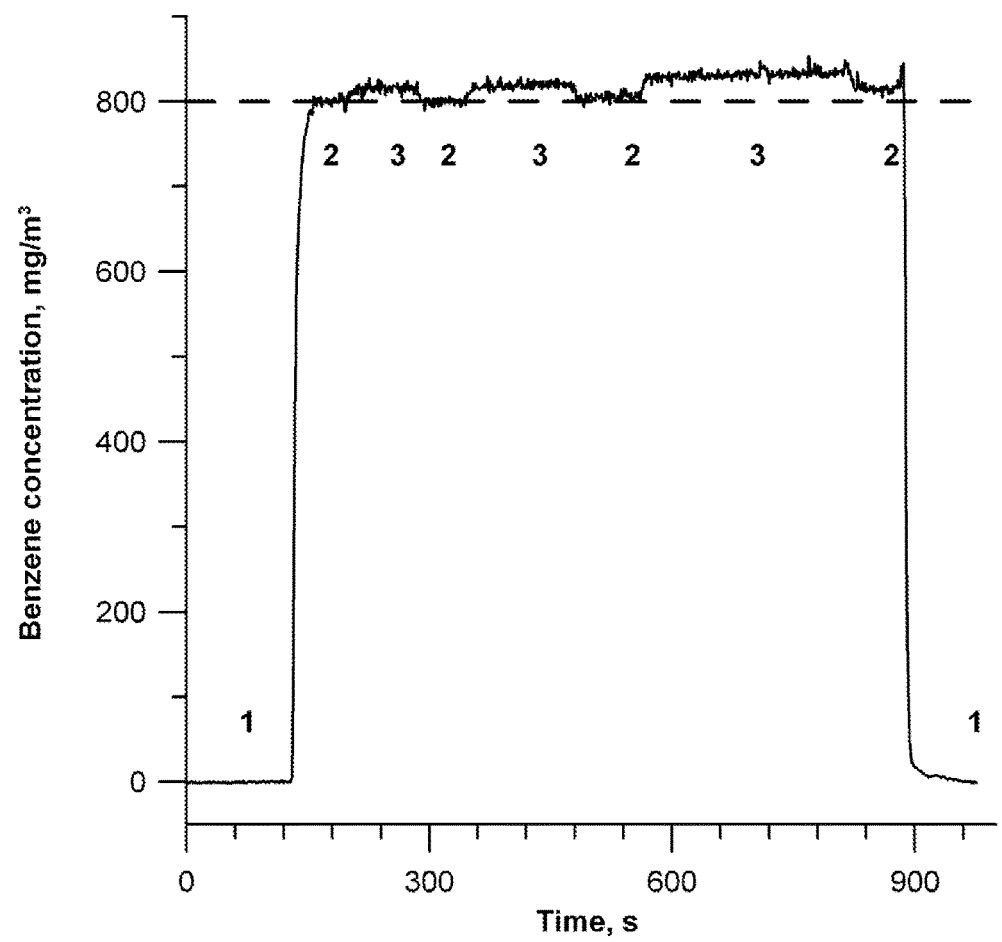

FIG. 3. The results of determination of mercury and benzene in the natural gas in one of Russian gas fields by transmitting the natural gas into an analytical cell of the absorption analyzer 1—through a filter with activated charcoal, which absorbs the mercury and benzene, 2—through a filter that absorbs only mercury, 3—directly with no filters.

Absorption analyzer shown at the block diagram (FIG. 1) consists of the spectral lamp 1, means of electrical discharge excitation 2, the magnet 3, the modulator of radiation polarization consisting of photoelastic modulator 4 with a quartz generator 5 and a polarizer 6, the analytical cell 7, the photodetector 8, and the signal processing unit 9. The gas system of the analyzer comprises the sampling port 10, three gas channels, one of which has the filter 11, which removes mercury and benzene from the gas stream, the other is directly connected to the sampling port 10 and to one of gas ports of the gas channels selector 13, and the third one has the filter 12 which removes mercury from the gas stream, and the gas channels selector 13, which alternately connects the gas channels to the input port of the analytical cell, and the output system 14 connected to the output port of the analytical cell.

Means of electrical discharge excitation 2 can be made as electrodes installed on the discharge cavity of the spectral lamp and connected to the high frequency excitation generator.

The analytical cell 7 can be made as a closed volume with the input port and the output port used for feeding and removing the sample gas, and the probing radiation passes through this volume multiple times by means of a system of mirrors. In a particular example, the use of multipath analytical cell with an equivalent length of 960 cm at allows to increase the measurement sensitivity 24 times relative to a length of one path of 40 cm with just a slight decrease of the intensity of the probing radiation.

The magnet is made of a material with high magnetic remanence magnetization in the form of two discs parted by a separator. The discharge cavity of the spectral lamp 1 is placed in the gap between the discs. Discs are magnetized so that the gap side of the one is the south pole, and the gap side of the other—the north pole. For coupling radiation out of the spectral lamp 1 one of the discs has a hole that allows to extract the radiation along the lines of magnetic force towards the optical axis.

The spectral lamp 1 design and methods of its connection to the exciter generator are discussed in detail in (4).

The signal-processing unit 9 contains amplifiers and detectors that filter signals at the modulation frequency and at direct current. After analog-to-digital conversion these signals come to the microprocessor for further signal processing, formation of an analytical signal and display of the measured mercury concentration in the analytical cell.

If the input pressure of the sample gas at the sampling port 10 is equal to the exit pressure at the output system 14, for example, is equal to atmospheric pressure, then the sampling port 10 includes dust filter and communications to transport the sample gas, and the output system 14 includes a gas pump, for example, diaphragm pump, that provides intake of the sample gas from the point of interest and its pumping through analytical cell and output communications. If the input pressure of the sample gas at the sampling port 10 exceeds the exit pressure at the output system 14, the sampling port 10 comprises a reducer which reduces the sample gas pressure down to an acceptable level and provides the desired flow rate through the analytical cell 7. The output system 14 contains only communication for the disposal of sample gas after it has passed through the analytical cell.

The filter 11, which removes mercury and benzene from a stream of the sample gas is formed as a volume with input and output ports, filled with activated charcoal in granular form.

The filter 12, which removes mercury from the sample gas stream is formed as a volume having input and output ports, which has the fabric impregnated I+KI placed inside. The efficiency of such a filter is presented in Table 2, which shows the dependence of permeability rates for benzene and mercury versus time.

TABLE 2

| | Exposure time, hours | | | | | | |
|---|---|---|---|---|---|---|---|
| | 1 | 2 | 4 | 8 | 12 | 24 | 48 |
| Benzene Permeability Rate, % | 102 ± 2 | 100 ± 1 | 99 ± 1 | 98 ± 1 | 98 ± 1 | 101 ± 1 | 97 ± 1 |
| Mercury Permeability Rate, % | 0.04 ± 0.02 | 0.5 ± 0.3 | 0.7 ± 0.2 | 0.8 ± 0.2 | 0.8 ± 0.2 | 0.4 ± 0.2 | 0.9 ± 0.2 |

From the results given in Table 2, it follows that the mercury absorption filter efficiency is not less than 99%, the loss of benzene transmitted through the filter does not exceed 3%. Experience with this type of filters has shown that they are able to operate for a long time (at least a year).

Gas channels selector 13 can be made as a single four-way valve, which has three input ports connected to respective gas channels, and an output port connected to the input port of an analytical cell. The selector can be also made in the form of combinations of two and three-way valves.

Consider the analyzer operation with the spectral lamp with the isotope $^{204}$Hg, the spectral position of the resonance emission line of which does not coincide with the spectral position of the maximum absorption line profile of mercury and a local maximum of the absorption band of benzene. To determine the concentration of mercury and benzene three measurements are made. The first one is made with the sample gas passing through a channel with the filter 11 removing mercury and benzene. The resulting level is taken as a value of zero concentration of mercury and benzene. The second measurement is carried out with the sample gas passing through a channel with the filter 12 removing only mercury. The procedure of measurement is as follows. In a magnetic field of the magnet 3 the emission resonance line of mercury $\lambda$=254 nm is split into unshifted $\pi$-component and two shifted $\sigma$-components (FIG. 2). In the observation of the radiation spectral lamp 1 along lines of the magnetic field the components $\sigma_+$ and $\sigma_-$ are observed with circular polarization clockwise and counterclockwise, respectively. The magnitude of magnetic field is selected in such a way that $\sigma_+$ component is shifted into the area of the maximum of the resonance absorption line of mercury and thus this component performs a role of the analytical line. Other $\sigma$-component of the mercury emission line is at the slope of the mercury absorption line profile where the absorption cross section is less than its maximal value. The second component plays a role of the reference line. To separate the intensities of $\sigma_+$- and $\sigma_-$ components the photoelastic modulator 4 and the linear polarizer 6 are used. In the absence of mercury atoms in the analytical cell 7 the intensity of $\sigma_+$ and $\sigma_-$-components are almost equal. In the presence of absorbing atoms the intensity of $\sigma_+$ component decreases as its spectral position gets into the absorption maximum, and the intensity of $\sigma$-component remains almost the same since it is in a region where the absorption cross section is less than the maximal value. As a result, there is a frequency modulation signal $S_\omega$, related to concentration of the atoms in the analytical cell. To ensure the selectivity the signal $S_0$ is used as the normalization signal, which is proportional to the direct current of the photodetector 8. The signals $S_\omega$ and $S_0$ are separated in the signal processing unit 9, and the signal $S=S_\omega/S_0$ is calculated. The result of the second measurement $S_2$ is associated with the signal S by the following relation [5]:

$$S_2 = -\frac{b}{2}\ln((b-S)/(b+S)) \quad (1)$$

where b is a normalization constant that depends on the parameters of the analyzer. Then, the concentration of mercury atoms in the sample gas $C_{Hg}$ is associated with the received signal $S_2$ by a simple equation:

$$C_{Hg} a_{Hg} S_2 \quad (2)$$

where $a_{Hg}=1/\Delta Q_{Hg}L$ is a calibration coefficient determined during the calibration of the analyzer for mercury, $\Delta Q_{Hg}$ is the differential absorption cross section of $\sigma_-$ and $\sigma_+$-components by mercury atoms, L is the length of the analytical cell.

The third measurement is made while the sample gas passing through a channel with no filter installed. During the processing using the above-stated algorithm, an analytical signal $S_3$ is obtained which is the sum of the analytical signal $S_{Hg}$ produced by mercury and $S_{benzene}$ produced by benzene:

$$S_3 = S_{Hg} + S_{benzene} \quad (3)$$

Because the analytical signal produced by mercury is obtained in the second measurement, the concentration of benzene $C_{benzene}$ is defined as follows:

$$C_{benzene} = a_{benzene}(S_3 - S_2) \quad (4),$$

where $a_{benzene}=1/\Delta Q_{benzene}L$ is a calibration coefficient determined during the calibration of the analyzer for benzene, $\Delta Q_{benzene}$ is a differential absorption cross section of $\sigma_+$- and $\sigma_-$-component by benzene molecules, L is the length of the analytical cell.

For the analyzer with a spectral lamp enriched by mercury isotope $^{204}$Hg, the following analytical characteristics were obtained:
- the detection limit (criterion 3$\sigma$ noise for a blank signal):
  - for benzene 1 mg/m3 at 1 second signal averaging and 0.2 mg/m3 at 30 seconds averaging, which is below the Occupational Exposure Limit of benzene concentration in the air of industrial zone (3.2 mg/m3)
  - for mercury 2 ng/m3 at 1 second signal averaging and 0.6 ng/m3 at 30 seconds averaging, which is below its background level in the ambient air (1-2 ng/m3).

The dynamic range of measured concentrations was about $10^4$.

The operation of the absorption analyzer was demonstrated by determination of mercury and benzene in one of the gas fields in Russia. Gas was taken to a separator, in which various impurities were removed from natural gas, and was fed to the analyzer. The measurement results are shown in FIG. 3. It is seen from the data provided, the concentration of benzene obtained using the developed analyzer amounted to 800±10 mg/m3, which is in good agreement with the data obtained by gas chromatography for the natural gas at the point of sampling (800 mg/m3).

Thus, the present invention allows to create an absorption analyzer, which can be used to determine mercury below its background level in the air and benzene below its Occupational Exposure Limit; to reduce the detection limit of benzene by using absorption spectroscopy with the direct Zeeman effect and multipath cell; to reduce the detection limit due to enriching mercury in the spectral lamp with mercury isotope with an even number of neutrons.

REFERENCES

1. T. Hadeishi, H. Koizumi, R. D. McLaughlin and J. E. Millaud, Tunable atomic line molecular (TALM) spectrometer, Spectrochim. Acta Part B 37 (1982) 501-509.
2. Hadeishi T. The, McLaughlin has the RD, the J G Conway, NH, the DR by Scott, the Selection of atomic emission lines for tunable atomic spectrometry Molecular line of benzene, Anal. Chem. 55 (1983), 1517-1519.
3. D R Scott, R L Hedgecoke, Laboratory evaluation of tunable atomic line molecular spectrometers for benzene analysis, Project summary EPA-600/S4-84-030, 1984.
4. Patent RU No. 2373522. Atomic Absorption Mercury Analyzer.
5. A. A. Ganeev, S. E. Sholupov, M. N. Slyadnev. Zeeman modulation polarization spectroscopy as a variant of atomic absorption analysis: opportunities and limitations, J. of Analytical Chemistry, 51 (1996), N28, 855-864.
6. 11. S. Fallya, M. Carleera, A. C. Vandaele, UV Fourier transform absorption cross sections of benzene, toluene, meta-, ortho-, and para-xylene, Journal of Quantitative Spectroscopy and Radiative Transfer 110 (2009) 766-782.

The invention claimed is:

1. An apparatus comprising:
an absorption analyzer, wherein the absorption analyzer includes:
a spectral lamp,
wherein the spectral lamp includes buffer gas and mercury,
wherein the spectral lamp includes a discharge cavity,
wherein the discharge cavity includes electrodes connected to a high frequency excitation generator,
wherein the discharge cavity is positioned between magnet poles,
a photoelastic modulator,
a photodetector,
a signal processing unit,
a polarizer,
an analytical cell,
wherein the spectral lamp, photoelastic modulator, and polarizer are in optical connection with the analytical cell,
wherein the analytical cell is in optical connection with the photodetector,
wherein the photodetector detects radiation from the spectral lamp that passes through the photoelastic modulator, polarizer, and the analytical cell and generates analytical signals, corresponding to sensed radiation, which are provided to the signal processing unit,
a gas system,
wherein the gas system comprises at least three gas channels, a sampling port, an input port of the analytical cell, and a gas channels selector,
wherein at least one of the gas channels is operative to remove benzene from a gas stream,
wherein at least one of the gas channels is operative to remove mercury from the gas stream,
wherein at least one of the gas channels is permeable for mercury,
wherein at least one of the gas channels is permeable for benzene,
wherein at least one of the gas channels has known different permeability rates for mercury and benzene,
wherein the sampling port is operatively fluid connectable with the input port of the analytical cell through the at least three gas channels and the gas channels selector,
wherein the gas channels selector is selectively operative to connect the sampling port and the input port through any selected one of the at least three gas channels,
wherein the signal processing unit is operative responsive to the analytical signals received when the analytical cell has been connected separately to each of the at least three gas channels, to thereafter output concentration signals, wherein the concentration signals are representative of mercury concentration or benzene concentration of sample gas in the analytical cell.

2. The apparatus of claim 1,
wherein the mercury included in the spectral lamp includes mercury enriched with at least one mercury isotope,
wherein the at least one mercury isotope contains an even number of neutrons,
wherein the mercury included in the spectral lamp is comprised of at least 50% of the at least one mercury isotope.

3. The apparatus of claim 2,
wherein the gas channels selector selectively is operative to:
a) in a first condition direct gas from the sampling port through a first gas channel that removes mercury but not benzene from the gas,
b) in a second condition, direct gas from the sampling port through a second gas channel that removes benzene but not mercury from the gas, and not concurrently through the first gas channel,
c) in a third condition, direct gas from the sampling port through a third gas channel that removes both mercury and benzene from the gas, and not concurrently through the first and second gas channels,
wherein the signal processing unit is operative to determine the concentration of mercury or benzene in the sample gas in the analytical cell from the analytical signals provided when the gas channel selector has been in each of the first, second, and third conditions.

4. The apparatus of claim 1,
wherein the analytical cell contains a system of mirrors,
wherein the system of mirrors direct the radiation through a plurality of paths within the analytical cell,
whereby the directed radiation results in an increase in measurement sensitivity of the photodetector.

5. The apparatus of claim 4,
wherein the gas channels selector is selectively operative to:
a) in a first condition direct gas from the sampling port through a first gas channel that removes mercury from the gas,
b) in a second condition, direct gas from the sampling port through a second gas channel that removes benzene from the gas, and not concurrently through the first gas channel,
c) in a third condition, direct gas from the sampling port through a third gas channel that removes mercury and benzene from the gas, and not concurrently through the first and second gas channels,
wherein the signal processing unit is operative to determine the concentration of mercury or benzene in the sample gas in the analytical cell from the analytical signals provided when the gas selector has been in each of the first, second and third conditions.

6. The apparatus of claim 1,
wherein the gas channels selector selectively is operative to:
a) in a first condition direct gas from the sampling port through a first gas channel that removes mercury but not benzene from the gas,
b) in a second condition, direct gas from the sampling port through a second gas channel that removes benzene but not mercury from the gas, and not concurrently through the first gas channel,
c) in a third condition, direct gas from the sampling port through a third gas channel that removes both mercury and benzene from the gas, and not concurrently through the first and second gas channels, wherein the signal processing unit is operative to determine the concentration of mercury or benzene in the sample gas in the analytical cell from the analytical signals provided when the gas channel selector has been in each of the first, second, and third conditions.

7. A method comprising:
a) injecting a sample into a sample port of an absorption analyzer,
   wherein the absorption analyzer includes:
   a spectral lamp,
      wherein the spectral lamp includes buffer gas and mercury,
      wherein the spectral lamp includes a discharge cavity,
      wherein the discharge cavity includes electrodes connected to a high frequency excitation generator,
      wherein the discharge cavity is positioned between magnet poles,
   a photoelastic modulator,
   a photodetector,
   a signal processing unit,
   a polarizer,
   an analytical cell,
      wherein the spectral lamp, photoelastic modulator, and polarizer are in optical connection with the analytical cell,
      wherein the analytical cell is in optical connection with the photodetector,
      wherein the photodetector detects radiation from the spectral lamp that passes through the photoelastic modulator, polarizer, and the analytical cell and generates analytical signals, corresponding to sensed radiation, which are provided to the signal processing unit,
      wherein the signal processing unit is operative to output concentration signals responsive to the analytical signals, wherein the concentration signals are representative of mercury concentration or benzene concentration of gas from the sample in the analytical cell,
   a gas system,
      wherein the gas system comprises at least three gas channels, a sampling port, an input port of the analytical cell, and a gas channels selector,
      wherein at least one of the gas channels is operative to remove benzene from a gas stream,
      wherein at least one of the gas channels is operative to remove mercury from the gas stream,
      wherein at least one of the gas channels is permeable for mercury,
      wherein at least one of the gas channels is permeable for benzene,
      wherein at least one of the gas channels has known different permeability rates for mercury and benzene,
      wherein the sampling port is operatively fluid connectable with the input port of the analytical cell through the at least three gas channels and the gas channels selector,
      wherein the gas channels selector is selectively operative to connect the sampling port and the input port through any selected one of the at least three gas channels,
b) selecting through the operation of the gas channels selector to connect the sampling port through each of the at least three gas channels with the analytical cell at different times,
   wherein subsequent to (b) the signal processing unit provides an output signal corresponding to mercury or benzene concentration of gas from the sample.

8. The method of claim 7, wherein in (a), the mercury included in the spectral lamp includes mercury enriched with at least one mercury isotope,
   wherein the at least one mercury isotope contains an even number of neutrons,
   wherein the mercury included in the spectral lamp is comprised of at least 50% of the at least one mercury isotope.

9. The method of claim 8, wherein in (b), the selecting through the operation of the gas channel selector comprises:
   i. directing gas from the sampling port through a first gas channel that removes mercury but not benzene from the gas,
   ii. not concurrently with (i), directing gas from the sampling port through a second gas channel that removes benzene but not mercury from the gas, and
   iii. not concurrently with (i) or (ii), directing gas from the sampling port through a third gas channel that removes both mercury and benzene from the gas.

10. The method of claim 7, wherein in (a), the analytical cell contains a system of mirrors,
   wherein the system of mirrors direct the radiation through a plurality of paths within the analytical cell,
   whereby the directed radiation results in an increase in measurement sensitivity of the photodetector.

11. The method of claim 10, wherein in (b), the selecting through the operation of the gas channel selector comprises:
   i. directing gas from the sampling port through a first gas channel that removes mercury but not benzene from the gas,
   ii. not concurrently with (i), directing gas from the sampling port through a second gas channel that removes benzene but not mercury from the gas, and
   iii. not concurrently with (i) or (ii), directing gas from the sampling port through a third gas channel that removes both mercury and benzene from the gas.

12. The method of claim 7, wherein in (b), the selecting through the operation of the gas channel selector comprises:
   i. directing gas from the sampling port through a first gas channel that removes mercury but not benzene from the gas,
   ii. not concurrently with (i), directing gas from the sampling port through a second gas channel that removes benzene but not mercury from the gas, and
   iii. not concurrently with (i) or (ii), directing gas from the sampling port through a third gas channel that removes both mercury and benzene from the gas.

* * * * *